United States Patent
Di Lullo et al.

(10) Patent No.: US 9,995,435 B2
(45) Date of Patent: Jun. 12, 2018

(54) METHOD FOR HINDERING NON-AUTHORISED WITHDRAWAL OF A LIQUID FROM AT LEAST ONE OFFTAKE CONDUIT CONNECTED TO A MAIN CONDUIT FOR THE TRANSPORT OF THE AFOREMENTIONED LIQUID, IN PARTICULAR A MIXTURE OF HYDROCARBONS AND WATER

(71) Applicant: ENI S.p.A., Rome (IT)

(72) Inventors: Alberto Giulio Di Lullo, Tribiano (IT); Giambattista De Ghetto, San Donato Milanese (IT)

(73) Assignee: ENI S.p.A., Rome (IT)

( * ) Notice: Subject to any disclaimer, the term of this patent is extended or adjusted under 35 U.S.C. 154(b) by 0 days. days.

(21) Appl. No.: 15/121,192

(22) PCT Filed: Feb. 20, 2015

(86) PCT No.: PCT/IT2015/000048
§ 371 (c)(1),
(2) Date: Aug. 24, 2016

(87) PCT Pub. No.: WO2015/128890
PCT Pub. Date: Sep. 3, 2015

(65) Prior Publication Data
US 2016/0369948 A1    Dec. 22, 2016

(30) Foreign Application Priority Data
Feb. 26, 2014  (IT) .............................. MI2014A0293

(51) Int. Cl.
*F17D 5/06* (2006.01)
*F17D 1/00* (2006.01)
(Continued)

(52) U.S. Cl.
CPC ............... *F17D 5/06* (2013.01); *F17D 1/005* (2013.01); *F17D 3/01* (2013.01); *F17D 5/005* (2013.01); *F17D 5/02* (2013.01); *G01N 15/0606* (2013.01)

(58) Field of Classification Search
None
See application file for complete search history.

(56) References Cited

U.S. PATENT DOCUMENTS 3,848,458 A * 11/1974 Soya ...................... G01M 3/005
340/605
6,241,028 B1 * 6/2001 Bijleveld ................ E21B 23/00
175/40
(Continued)

FOREIGN PATENT DOCUMENTS

WO    WO 02/061412 A2    8/2002
WO    WO 2006/081671 A1    8/2006
(Continued)

OTHER PUBLICATIONS

International Search Report and Written Opinion of the International Searching Authority dated Dec. 3, 2015 in PCT/IT2015/000048 filed Feb. 20, 2015.

*Primary Examiner* — Paul West
*Assistant Examiner* — Mark A Shabman
(74) *Attorney, Agent, or Firm* — Oblon, McClelland, Maier & Neustadt, L.L.P.

(57) ABSTRACT

Method for hindering the non-authorized withdrawal of a liquid from at least one offtake conduit connected to a main conduit for the transport of the aforementioned liquid, in particular a mixture of hydrocarbons and water, the main conduit having an inlet port and at least one outlet port between which the liquid flows, the method comprising the step of: introducing a plurality of solid objects into the main conduit through the at least one inlet port, the plurality of
(Continued)

introduced solid objects having weight, dimensions and density such as to be transportable towards the at least one outlet port by the main flow of the liquid and such as to be able to be possibly captured by the offtake flow of the liquid directed towards the offtake conduit, and such as to be able to possibly at least partially obstruct such an offtake conduit.

12 Claims, 2 Drawing Sheets

(51) Int. Cl.
    *F17D 3/01*     (2006.01)
    *F17D 5/00*     (2006.01)
    *F17D 5/02*     (2006.01)
    *G01N 15/06*     (2006.01)

(56) References Cited

U.S. PATENT DOCUMENTS

| | | | |
|---|---|---|---|
| 9,234,812 B2* | 1/2016 | Krywyj | G01M 3/005 |
| 9,651,445 B2* | 5/2017 | McIntyre | G01M 3/005 |
| 2003/0164698 A1 | 9/2003 | Paulson et al. | |
| 2003/0173959 A1 | 9/2003 | Paulson et al. | |
| 2004/0025607 A1* | 2/2004 | Rantala | G01L 5/008 73/866.5 |
| 2008/0204008 A1* | 8/2008 | Paulson | F16L 55/38 324/220 |
| 2009/0224915 A1* | 9/2009 | Angell | G06Q 10/06 340/572.1 |
| 2010/0064775 A1* | 3/2010 | Ben-Mansour | G01M 3/22 73/40.5 A |
| 2013/0291635 A1* | 11/2013 | Di Lullo | G01M 3/246 73/488 |
| 2014/0123759 A1 | 5/2014 | Minto et al. | |

FOREIGN PATENT DOCUMENTS

WO    WO 2012/010474 A1    1/2012
WO    WO 2012/175954 A1    12/2012

* cited by examiner

METHOD FOR HINDERING NON-AUTHORISED WITHDRAWAL OF A LIQUID FROM AT LEAST ONE OFFTAKE CONDUIT CONNECTED TO A MAIN CONDUIT FOR THE TRANSPORT OF THE AFOREMENTIONED LIQUID, IN PARTICULAR A MIXTURE OF HYDROCARBONS AND WATER

The present invention refers to a method for hindering non-authorised withdrawal of a liquid from at least one offtake conduit that is connected to a main conduit for the transport of the aforementioned liquid, in particular a mixture of hydrocarbons and water.

Nowadays, it is common to transport hydrocarbon and water-based liquids from one place to another by means of conduits or pipelines that can be several hundreds of kilometers long.

Where possible, such conduits are periodically guarded by security guards for almost their entire extension not only in order to prevent illegal activities or vandalism, but also to monitor the integrity of the conduit.

However, the aforementioned conduits can have sections that remain completely unguarded, in particular in correspondence of territories that are difficult to access, like for example swamps, sea beds, especially at great depths, deserts and so on.

In the case of non-underwater conduits, these sections that are not guarded sometimes are affected by actions of non-authorised or illegal withdrawal of the liquid transported in the main conduit.

Such non-authorised actions are carried out by applying, to the main conduits, offtake conduits, in which part of the liquid passing through the main conduit is conveyed.

Frequently, the aforementioned offtake conduits have a circular section with a diameter that is comprised between one and four inches. It is less common, but possible, for such offtake conduits to have a greater diameter.

Acts of unauthorised withdrawal, often called illegal bunkering, has become increasingly common over the last few years and represents a large source of financial loss for companies in charge of extracting and/or distributing and marketing hydrocarbons.

Moreover, illegal withdrawal is very often accompanied by spilling the sample material into the environment and/or, in the case of treatment of hydrocarbons in unauthorised or illegal plants, by the unauthorised disposal of waste products; such actions can cause huge damage to the environment.

Currently, in order to reduce the risk of these illegal withdrawal acts, surveillance and guarding of the territory is increased.

Unfortunately, however, this type of countermeasures are not always effective, since the monitoring of some inaccessible and dangerous territories is difficult to carry out and it can neither be continuous nor rapid to carry out during illegal bunkering. Moreover, the people who carry out the actions of illegal bunkering are often able to hide or disguise the offtake point so as to make it difficult for security staff to detect them with external inspections of the conduits.

Also known are remote systems for monitoring the surface integrity of the main conduit comprising a plurality of sensors that are suitable for detecting and localising the cuts made on the conduit for the subsequent application of the offtake conduits.

However, these remote monitoring systems are not very effective, in particular for bunkering of less than 3-4% of the transported product, or they can easily undergo sabotaging, making it difficult for them to be continuously maintained; moreover, they do not hinder bunkering but only detect and, only for some technologies, localise the possible presence of the offtake conduit.

The purpose of the present invention is to avoid the drawbacks mentioned above and, in particular, to conceive a method that is capable of discouraging acts of unauthorised bunkering without implementing aggressive actions of patrolling or surveillance of the territory.

Another purpose of the present invention is to provide a method that makes it possible to at least partially obstruct and possibly detect the presence of at least one offtake conduit, connected to a main conduit for transporting a liquid, in an extremely simple, cost-effective and particularly functional manner.

These and other purposes according to the present invention are achieved by making a method for hindering non-authorised withdrawal of a liquid from at least one offtake conduit connected to a main conduit for the transport of the aforementioned liquid, in particular a mixture of hydrocarbons and water, as outlined in claim 1.

Further characteristics of the method for hindering the non-authorised withdrawal of a liquid from at least one offtake conduit connected to a main conduit for the transporting the aforementioned liquid, in particular a mixture of hydrocarbons and water, are object of the dependent claims.

The characteristics and the advantages of a method for hindering the non-authorised withdrawal of a liquid from at least one offtake conduit connected to a main conduit for the transport of the aforementioned liquid, in particular a mixture of hydrocarbons and water, according to the present invention shall become clearer from the following description, given as an example and not for limiting purposes, with reference to the attached schematic drawings, in which.

Figure 1:
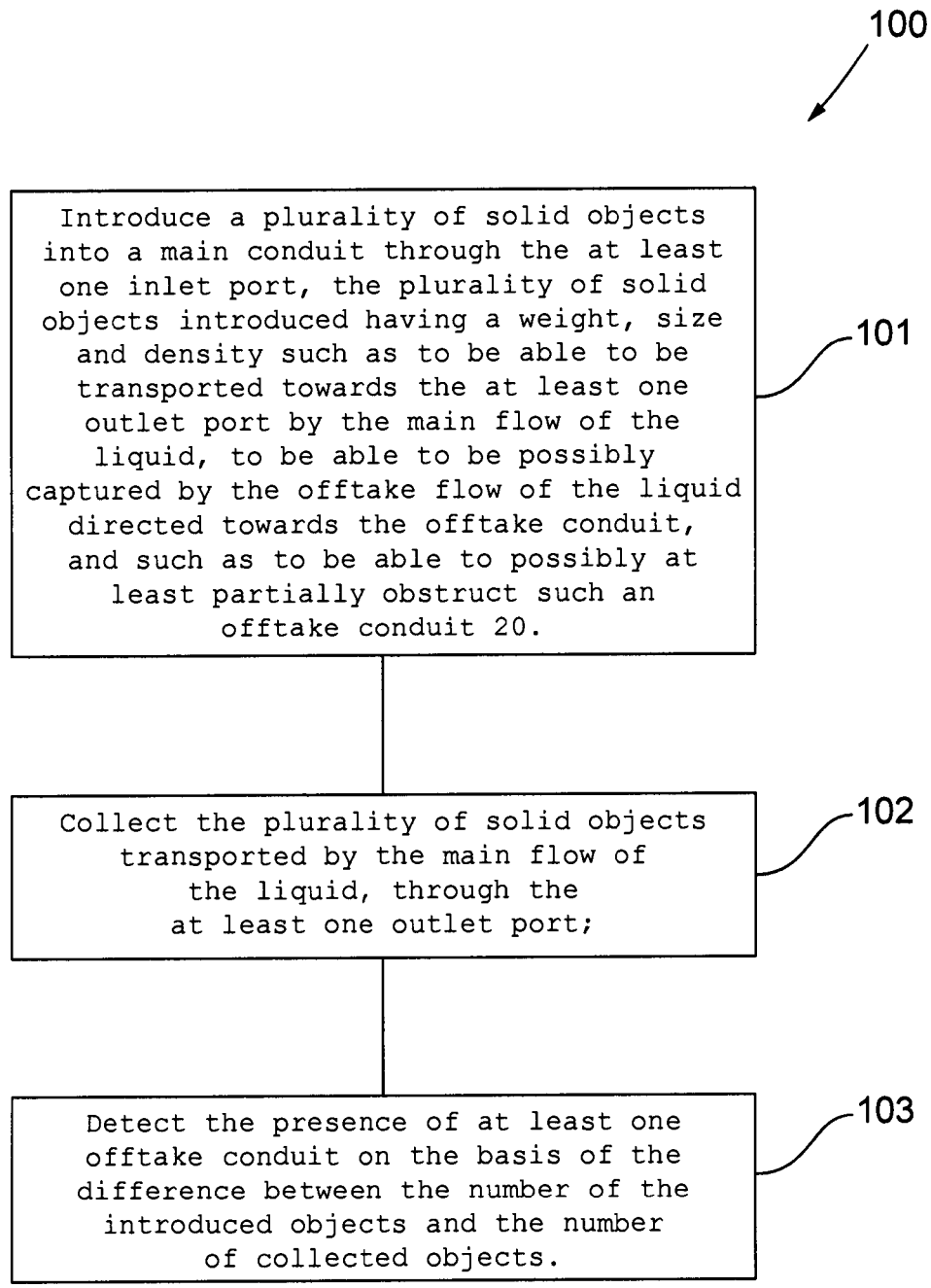
FIG. 1 is a flow chart that represents the steps of an embodiment of the method for hindering the non-authorised withdrawal of a liquid from at least one offtake conduit connected to a main conduit for the transport of the aforementioned liquid, in particular a mixture of hydrocarbons and water, according to the present invention.
Figure 2:
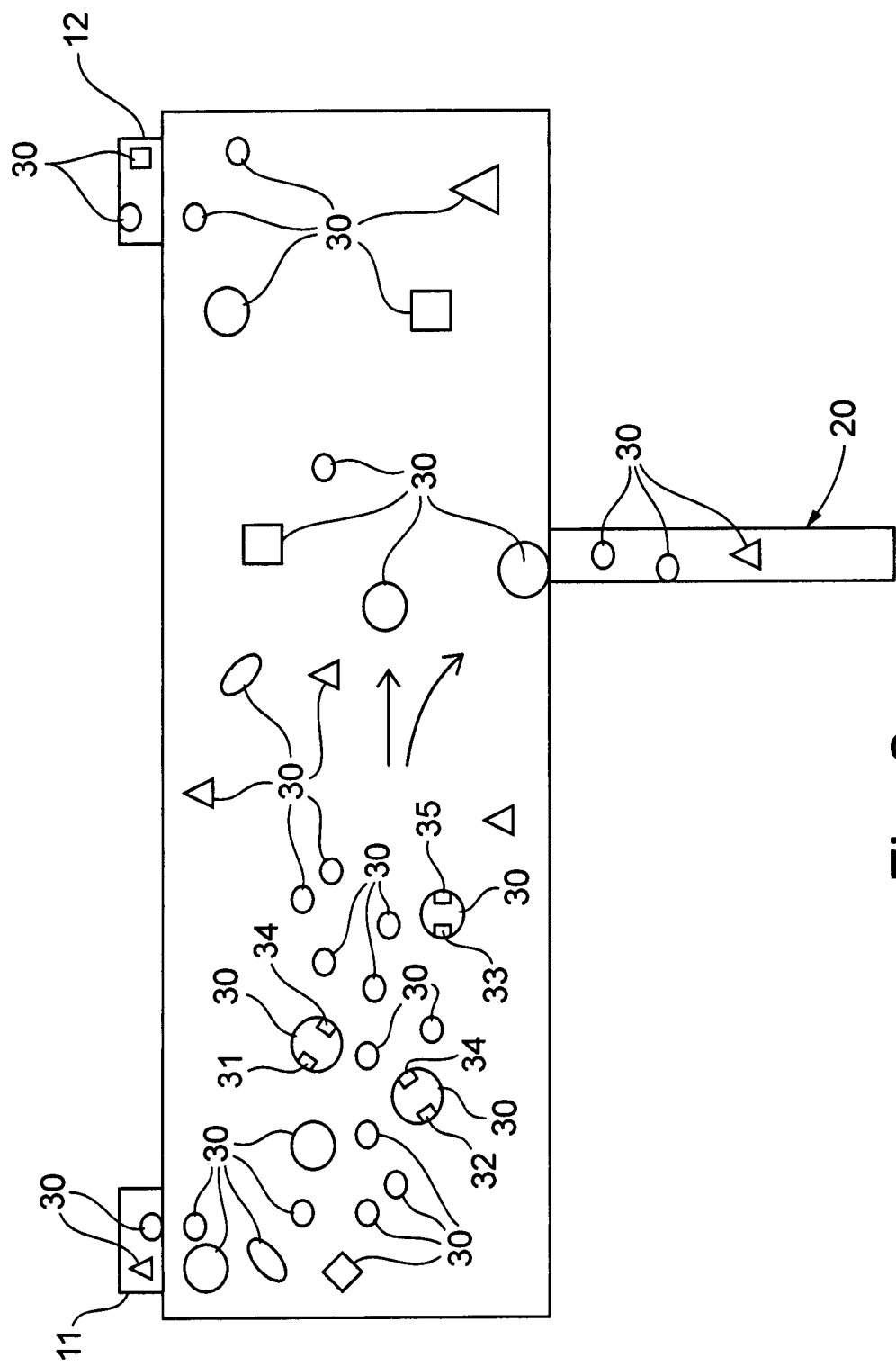
FIG. 2 is a schematic view of an application scenario of the method of FIG. 1.

With reference to the figures, a method is shown, wholly indicated with reference numeral 100, for hindering the non-authorised withdrawal of a liquid from at least one offtake conduit connected to a main conduit for the transport of the aforementioned liquid. Such a method 100 can be applied to transportation lines for liquids, in particular mixtures of hydrocarbons and water, with possible presence of gas.

In detail, the volumetric fraction of water in the aforementioned mixtures is comprised between 0% and 100%.

Differently, the volumetric fraction occupied by the free gas in the conduit, or rather the ratio between the volume of gas and the sum of the volume of the liquid and the volume of gas, must be on average less than 0.7.

These transport lines can be made up by both conduits that are suitable for being inspected inside them through devices called PIGs, and by conduits that cannot be internally inspected since they do not accept objects having an inner diameter equal to that of the conduit itself being introduced inside them.

In any case, the main conduit 10 of one line for transporting liquid hydrocarbons has at least one inlet port 11 and at least one outlet port 12 between which the liquid flows.

As anticipated above, the at least one offtake conduit 20 is connected to the main conduit 10 so that part of the flow of liquid passing through the main conduit 10 is directed towards the offtake conduit 20 itself. The offtake conduit 20, then, ends in a collection station where the illegally taken liquid is accumulated.

The method 100 according to the present invention comprises the step in which a plurality of solid objects 30 is introduced 101 in the main conduit 10 through the at least one inlet port 11.

These introduced solid objects 30 have, in detail, weight, size and density such as to be transportable towards the at least one outlet port 12 by the flow of the passing liquid through the conduit, such as to be able to be possibly conveyed towards the offtake conduit 20 and such as to be able to possibly at least partially obstruct such an offtake conduit 20.

In one preferred embodiment of the present invention, after the introduction step 101, through the at least one outlet port 12, the plurality of objects 30 transported by the liquid is collected 102 and the presence of at least one offtake conduit 20 is detected 103 on the basis of the difference between the number of the introduced objects and the number of collected objects.

In particular, in the case in which an offtake conduit 20 has been applied to the main conduit 10, the solid objects 30 introduced in the main conduit 10, arrived at the offtake conduit 20, can be captured by the flow of liquid directed towards the offtake conduit 20 itself. In such a case, the captured objects 30 can get stuck at the port of the offtake conduit 20 at least partially obstructing it or they can penetrate inside it until coming out in the illegal collection station.

In any case, the introduced solid objects 30, which have not been captured by the flow directed towards the offtake conduit 20, arrive at the outlet port 12 of the main conduit 10. Therefore, if the number of the collected objects is different from the number of objects introduced, the presence of at least one offtake conduit 20 is detected.

Thanks to this detection it is then possible to actuate the procedures aimed at localising the detection conduit and removing it.

The steps of introducing 101 and collecting 102 the solid objects are carried out respectively by means of manual or automatic launching systems and collection systems, like for example, a pig receiver.

Preferably, the introduced solid objects have dimensions and/or weight and/or density that are different from one another.

In such a way the probability of detecting the unauthorised bunkering is increased, since it is more probable that, in the case in which offtake conduits are installed at different heights with respect to the circumference of the main conduit, some of the introduced objects are captured by the offtake flow.

Preferably, the introduced solid objects have a density comprised between 0.5 and 1.2 $g/cm^3$.

In such a way the solid objects 30 can flow in the liquid through the main conduit 10 at different heights with respect to the circumference of the main conduit avoiding to accumulate towards the top or the bottom of such a conduit 10 if their density is respectively too low or too high. In particular, such solid objects 30 are preferably made up of a material or a combination of materials having a density that is substantially constant over time and that is capable of dissolving when in contact with the transported liquid for a long time, where by long time we mean in contact with the liquid for several weeks or months, much longer than the transit time of such solid material in the conduit in normal flow conditions.

In order to obtain a certain density, the solid objects can be made up of a combination of different materials that are dense to a greater or lesser extent with respect to the transported liquid.

Preferably, the solid objects can be made up of a combination of plastic, polymeric or elastomeric materials, which are full or hollow on the inside or in the form of filaments that are grouped in the desired shape.

Among the materials of polymeric or elastomeric nature, it is possible to select the material from polyurethanes, polyethylenes, polystyrenes, polyesters, acetals or mixtures thereof.

In one preferred embodiment, the material of polymeric or elastomeric nature used, is polyurethane.

Preferably, the polymeric or elastomeric material can undergo dissolving, depolymerisation or breakdown within a period of time comprised between 1 month and 6 months.

The solid objects moreover, can be preferably made up of a combination of natural materials, such as wood or cork covered with an impermeabilising layer so as to prevent the permeation of the substances transported in the conduit.

According to a further alternative, the solid objects can comprise a plurality of hollow glass micro-spheres, which are useful for reducing the density of the plastic material in a controlled and permanent manner. Preferably, the introduced solid objects have a section having its maximum dimension comprised between 3 cm and 12 cm. In such a way, the objects 30 are free to flow in the main conduit 10 and possibly at least partially obstruct the offtake conduit 20 in the case in which they are captured by the flow of liquid directed towards it.

Such solids can have different shapes, geometrically regular or irregular, and overall have a different section according to the observation plane.

Preferably, at least one of the solid objects 30 introduced in the main conduit is provided with a localisation module 31, for example a GPS localizer that is configured to send a localisation signal to a remote central unit (not illustrated), in a wireless manner, upon exit from the offtake conduit 20, should the at least one object provided with such a localisation module 31 be captured by the offtake flow.

In particular, the localisation signal is sent to a remote central unit through which an operator can localise the transmitting object, should it not be collected at the outlet port of the main conduit 10 and be, on the other hand, transported to the unauthorised collection station.

Preferably, at least one of the introduced solid objects 30 is provided with tracking means 32 that are intended—in use—for being released into the liquid upon exit from the offtake conduit 20, should the at least one object 30 provided with such tracking means 32 be captured from the offtake flow.

For example, the tracking means 32 can be Gadolinium salts of carboxylic acids.

Preferably, at least one of the solid objects 30 introduced is provided with contamination means 33 intended—in use—for being released into the liquid upon exit from the offtake conduit 20, should the at least one object 30 provided with such contamination means 33 be captured from the offtake flow.

For example, the contamination means 33 can be emulsifying agents or foaming substances or viscosizing substances and so on.

Preferably, in addition to the localisation module 31 or to the tracking means 32 or to the contamination means 33, at least one of the introduced solid objects is provided with acceleration or temperature or pressure sensors 34 that are adapted to detect the instant of the passage near to the offtake conduit 20, should the object 30 continue on its path in the main conduit 10 and is recovered at the end thereof, or the instant in which the object comes out from the offtake conduit 20.

In such a case the solid object 30 is moreover preferably provided with a wireless transmission system that is configured so as to communicate the detections of the aforementioned acceleration or temperature or pressure sensors 34.

According to one embodiment of the present invention, one or more pressure sensors or one or more hydrophones can be positioned at the ends of the conduit so as to make it possible to detect anomalies associated with the passage of the solid inside the offtake conduit 20. In such a case, the method 100 comprises the step in which the data relative to the detected anomalies are processed and the offtake conduit is localised based upon the aforementioned processed data.

According to one first alternative embodiment, preferably, in addition to the localisation module 31 or to the tracking means 32 or to the contamination means 33, at least one of the introduced solid objects is provided with a control unit 35 that is configured so as to activate the aforementioned localisation module 31 or to release the aforementioned tracking means 32 or contamination means 33 after a first predetermined time interval.

Such a first predetermined time interval, in particular, is set so as to be longer than the time estimated necessary for running the distance inside the main conduit between the inlet port and the outlet port.

According to a second alternative embodiment, preferably, in addition to the localisation module 31 or to the tracking means 32 or to the contamination means 33, at least one of the introduced solid objects is provided with a control unit 36 that is configured so as to activate the aforementioned localisation module 31 or to release the aforementioned tracking means 32 or contamination means 33 following the contact with the liquid for a long time, or rather if the presence of the liquid in contact with the object 30 is detected for a time interval that is greater than a second predetermined time interval. Such a contact time can be, for example, detected by measuring the electric conductivity, which is more effective for aqueous-based or electrically conductive fluids, and more effective in the case of hydrocarbon based fluids.

From the present description the characteristics of the method for hindering the non-authorised withdrawal of a liquid from at least one offtake conduit connected to a main conduit for the transport of the aforementioned liquid, object of the present invention are clear, just as the relative advantages are also clear.

Indeed, the method according to the present invention makes it possible to detect the presence of an unauthorised offtake conduit in a simple and cost-effective manner.

The aforementioned method does not require the conduits to be special in terms of mechanics or construction and, therefore, it can be applied also to pre-existing conduits, which have been repeatedly damaged and repaired.

With respect to the monitoring or remote localisation methods, the method according to the present invention has the advantage of directly interfering with illegal bunkering operations thus reducing the impact thereof through the partial or total obstruction of the withdrawal points.

With respect to the monitoring methods based on patrolling and guarding, the method according to the present invention has the advantage of not exposing security staffs to danger and of not requiring continuous movements on the territory.

Finally, the method according to the present invention is not in any way pollutant or harmful to the environment or to the health of the workers or of the people who commit the illegal withdrawal.

Finally, it is clear, that the method thus conceived can undergo numerous modifications and variants, all covered by the invention; moreover, all the details can be replaced by technically equivalent elements. In practice the materials used, as well as the dimensions, can be any, according to the technical requirements.

The invention claimed is:

1. A method for hindering a non-authorized offtake flow of a mixture of hydrocarbons and water or other liquid from a main conduit for the transport of said liquid, wherein said main conduit comprises an inlet port and an outlet port downstream of the inlet port between which said liquid flows, said method comprising:
    introducing a plurality of known number of solid objects having a section of maximum dimension of from 3 cm to 12 cm into said main conduit through the inlet port, said plurality of introduced solid objects having weight, size and density such as to be transported to the outlet port by a main flow of said liquid,
    collecting the solid objects transported by the main flow of said liquid to the outlet port;
    counting the number of solid objects collected at the outlet port;
    comparing the number of solid objects collected at the outlet port to the number introduced at the inlet port;
    detecting the presence of an offtake flow when the number of the collected objects is different from the number of the introduced objects.

2. The method according to claim 1, further comprising when the presence of an offtake flow is detected:
    localizing and removing the offtake conduit of the offtake flow.

3. The method of claim 1, further comprising when an offtake flow is present:
    capture of at least a portion of said plurality of introduced solid objects by the offtake flow of said liquid directed towards an offtake conduit, wherein the captured solid objects at least partially obstruct the offtake conduit.

4. The method according to claim 1, wherein said introduced solid objects have dimensions and/or weight and/or density different from each other.

5. The method according to claim 1, wherein a density of said introduced solid objects is between 0.5 and 1.2 g/cm$^3$.

6. The method according to claim 1, further comprising:
    introducing with the plurality of solid objects at least one solid object comprising a localization module configured to send a wireless localization signal to a remote control unit upon exit from an offtake conduit, when said at least one object provided with said localization module is captured by an offtake flow.

7. The method according to claim 6, wherein at least one of said introduced solid objects is provided with a control unit configured to activate said localization module after a time interval which is greater than a time estimated for the solid object to run the distance from the inlet port to the outlet port.

8. The method according to claim 1, further comprising:
introducing with the plurality of solid objects at least one solid object comprising a tracking means which is released into the liquid upon exit from an offtake conduit, when said at least one object provided with said tracking means is captured by an offtake flow.

9. The method according to claim 8, wherein at least one of said introduced solid objects is provided with a control unit configured to release said tracking means after a time interval which is greater than a time estimated for the solid object to run the distance from the inlet port to the outlet port.

10. The method according to claim 1, further comprising:
introducing with the plurality of solid objects at least one solid object comprising a contamination means which is released into the liquid upon exit from an offtake conduit, when the at least one object provided with such contamination is captured by an offtake flow.

11. The method according to claim 10, wherein at least one of said introduced solid objects is provided with a control unit configured to activate said contamination means after a time interval which is greater than a time estimated for the solid object to run the distance from the inlet port to the outlet port.

12. The method according to claim 1, further comprising:
introducing with the plurality of solid objects at least one solid object comprising acceleration or temperature or pressure sensors that detect the instant of the passage close to an offtake conduit or the instant of exit of the object from said offtake conduit based on a change in acceleration, temperature or pressure.

\* \* \* \* \*